US006813516B2

(12) United States Patent
Ujhelyi et al.

(10) Patent No.: US 6,813,516 B2
(45) Date of Patent: Nov. 2, 2004

(54) METHOD AND ARRANGEMENT FOR USING ATRIAL PACING TO PREVENT EARLY RECURRENCE OF ATRIAL FIBRILLATION

(75) Inventors: Michael R. Ujhelyi, Maple Grove, MN (US); David E. Euler, Minnetonka, MN (US); David A. Casavant, Reading, MA (US); Nirav V. Sheth, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

(21) Appl. No.: 10/062,126

(22) Filed: Jan. 31, 2002

(65) Prior Publication Data

US 2003/0144698 A1 Jul. 31, 2003

(51) Int. Cl.[7] ................................................ A61N 1/39
(52) U.S. Cl. ........................................................ 607/4
(58) Field of Search ........................ 607/4, 5, 9, 14–15

(56) References Cited

U.S. PATENT DOCUMENTS

| | | | | |
|---|---|---|---|---|
| 5,549,641 A | * | 8/1996 | Ayers et al. | 607/4 |
| 5,713,924 A | * | 2/1998 | Min et al. | 607/4 |
| 5,893,882 A | * | 4/1999 | Peterson et al. | 607/14 |
| 6,058,328 A | | 5/2000 | Levine et al. | 607/14 |
| 6,185,459 B1 | | 2/2001 | Mehra et al. | 607/14 |
| 2002/0147473 A1 | * | 10/2002 | Seim et al. | 607/14 |

FOREIGN PATENT DOCUMENTS

| WO | WO 99/47206 | * | 9/1999 | A61N/1/36 |
|---|---|---|---|---|
| WO | WO 00/78390 A1 | | 12/2000 | A61N/1/362 |

* cited by examiner

*Primary Examiner*—Carl Layno
(74) *Attorney, Agent, or Firm*—Michael C. Soldner; Girma Wolde-Michael

(57) ABSTRACT

A method for preventing early recurrence of atrial fibrillation by pacing a heart in AAI mode at a rate faster than the intrinsic rate for a selected period of time immediately after delivering therapy to terminate the fibrillation. Ventricular backup pacing in VVI mode may also be provided during the atrial pacing.

26 Claims, 2 Drawing Sheets

METHOD AND ARRANGEMENT FOR USING ATRIAL PACING TO PREVENT EARLY RECURRENCE OF ATRIAL FIBRILLATION

FIELD OF THE INVENTION

This invention relates to the field of pacemakers and pacing algorithms; and, in particular, to delivering atrial overdrive pacing to an atrium to decrease the recurrence of atrial fibrillation after the delivery of a therapy to terminate an atrial arrhythmia.

BACKGROUND OF THE INVENTION

Atrial fibrillation is probably the most common form of cardiac arrhythmia. Patients afflicted with atrial fibrillation generally experience rapid and irregular heartbeats and may even experience dizziness as a result of reduced cardiac output. Atrial fibrillation occurs suddenly and can be corrected by an electrical shock into the atria of the heart. Implantable atrial defibrillators detect the presence of atrial fibrillation and provide a single cardioverting pulse of electrical energy (or electrical shock) as the therapy. However, atrial fibrillation usually returns within minutes after delivery of the electrical therapy in about one-half of the patients with atrial fibrillation episodes.

One mechanism for preventing atrial fibrillation involves providing atrial overdrive pacing therapy. This type of therapy paces the right atrium at a rate faster than the atrial intrinsic rate for a predetermined period of time. The implanted device applies pacing pulses to the right atrium (referred to as "A pulses") at a time in the cardiac cycle that is just prior to the occurrence of a spontaneous atrial depolarization (referred to as a "P-wave"). Thus, in overdrive pacing, a sequence of A-pulses applied to the atrium causes the atrium to depolarize at a time in the cardiac cycle that is slightly before the spontaneous occurrence of the P-wave, thereby preventing the on-set of an atrial fibrillation episode.

During preventative atrial overdrive pacing, the ventricular rate of a patient may drop to an extremely low level. Thus, most implanted devices switch to a dual chamber pacing and sensing mode (DDI mode) and thereafter determine whether the on-set of atrial fibrillation was prevented. After a predetermined time of pacing in DDI mode, a normal pacing mode wherein the atria and ventricles are synchronized (DDD mode) is resumed. For a more detailed discussion and definition of the various pacing and sensing mode codes for implantable medical devices, reference is made to *The NASPE/BPEG Generic Pacemaker Code for Antibradyarrhythmia and Adaptive-Rate Pacing and Antitachyarrhythmia Devices*, by Bernstein, et.al., (NASPE in July, 1987), which is incorporated herein by reference.

The above approach presents several problems. First, when sustained high-rate atrial tachyarrhythmias are present, pacing in DDI mode can result in excessive high-rate ventricular pacing. This, in turn, causes patient discomfort, increases manifestations of heart failure symptoms, and may induce atrium or ventricular arrhythmias. Moreover, traditional pacing devices limit the pacing rate available in DDI mode such that rates are insufficient for overdrive pacing during high-rate atrial arrhythmias.

What is needed, therefore, is an improved system and method for preventing atrial fibrillation. The system is adapted to prevent re-occurrence of atrial fibrillation following shock delivery. Ideally, the therapy should take effect quickly and without an associated increase in ventricular pacing rates.

SUMMARY OF THE INVENTION

Various embodiments of the present invention are directed to addressing the above and other needs in connection with preventing early recurrence of atrial fibrillation by pacing a heart in an atrial overdrive mode for a selected period of time immediately after applying an electrical cardioverting therapy.

According to one embodiment of the invention, a system is provided for preventing the early reoccurrence of atrial fibrillation (ERAF) following cardioversion, defibrillation, or anti-tachy pacing (ATP) therapy in the atrium. After the delivery of such therapy, the device switches to a DDI mode for a predetermined number of cycles, which, in the preferred embodiment, is only a single cycle. This switch to DDI mode may occur without any substantial delivery following therapy delivery. Another mode switch then occurs to an AAI pacing mode with backup VVI pacing in the ventricle.

In one embodiment of the invention, a method of preventing ERAF is provided. The method includes utilizing an implanted medical device (IMD) to apply an ATP or high-voltage shock therapy to the atrium. Thereafter, the implanted medical device paces the heart with an atrial overdrive pacing therapy with backup ventricular pacing. Prior to this mode switch, one or more optional pacing cycles may be performed in DDI mode.

According to one aspect of the invention, atrial overdrive pacing with VVI backup may be performed for a user-selectable time and pacing rate. The rate may also optionally decrease over time so that the system reverts to a normal pacing rate in DDD mode after the predetermined time.

Yet another aspect of the invention involves terminating atrial overdrive pacing after a reoccurrence of atrial fibrillation is detected. Thereafter, appropriate therapy may be delivered, including ATP or high-voltage shock therapy. Additional aspects of the invention will be apparent to those skilled in the art from the following description and accompanying drawings.

BRIEF DESCRIPTION OF THE DRAWINGS

The invention may be more completely understood in consideration of the following detailed description of various embodiments of the invention in connection with the accompanying drawings, in which.

Figure 1:
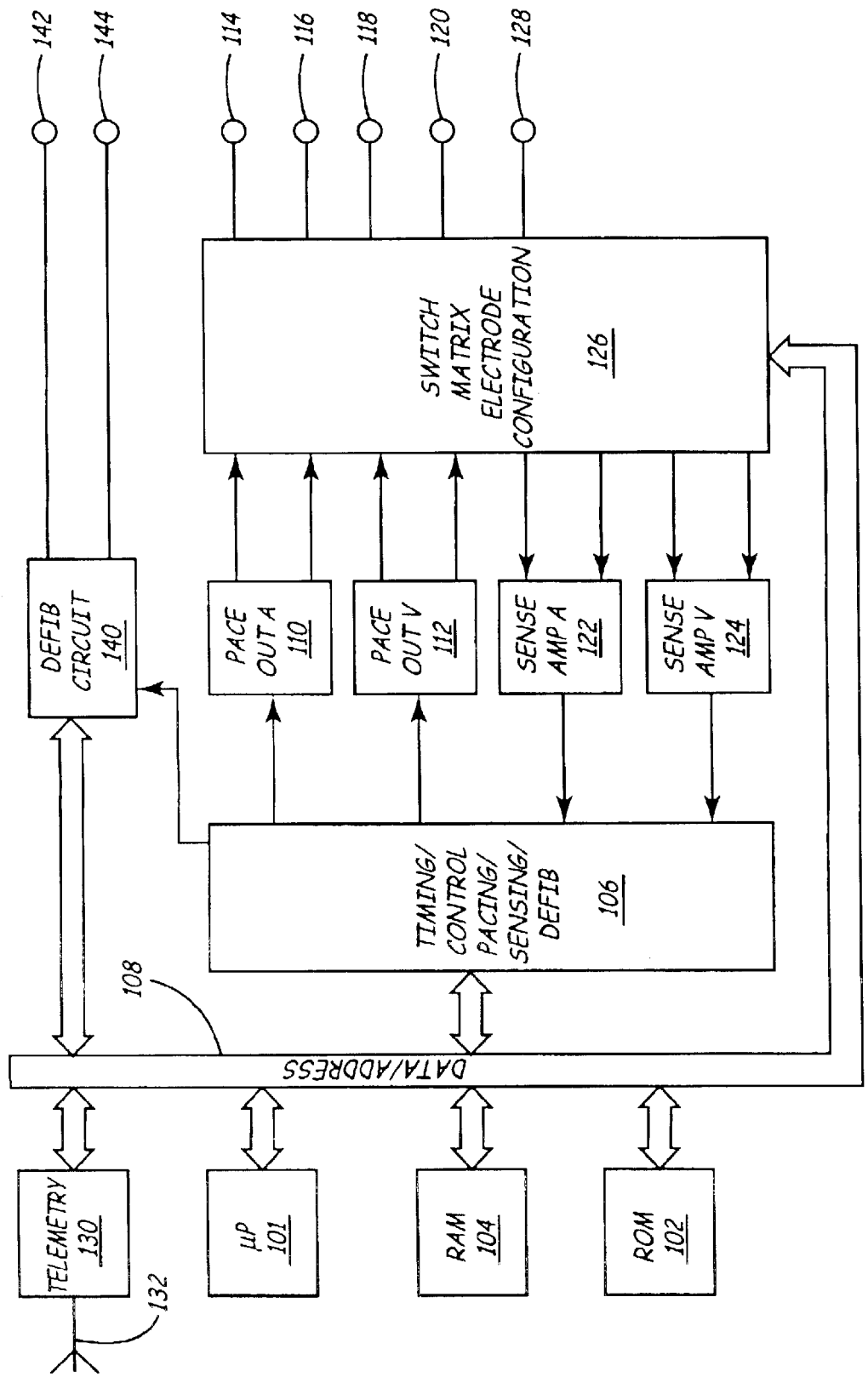
FIG. 1 illustrates a block diagram of an implanted medical device configured to apply overdrive pacing according to an example embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a method for preventing early recurrence of atrial fibrillation. The invention includes a novel pacing mode that provides atrial overdrive pacing with backup ventricular pacing for a selected period of time immediately after applying anti-tachy pacing (ATP), cardioverting, or any type of high-voltage therapy. During the atrial overdrive pacing, the implanted medical device performs sensing in both the atria and ventricles.

In an exemplary embodiment, an implanted medical device includes an atrial overdrive pacing mechanism that is triggered by an electrical cardioverting therapy or ATP therapy. Immediately after the electrical therapy, the implanted device automatically switches to a predetermined number of cycles of DDI sensing mode, which in one embodiment, includes only a single cycle. This approach provides immediate atrial pacing before the implanted device reverts to other programmed pacing modes. It may be noted that this immediate switch to DDI mode following high-voltage therapy differs from the operation of all known traditional pacing devices, which revert to VVI mode immediately following delivery of cardioversion or defibrillation therapy.

After the predetermined number of DDI cycles have been delivered, the pacing algorithm switches to an AAI pacing mode with backup ventricular pacing. Because ventricular pacing is backup only, excessive high-rate ventricular pacing is eliminated. Operation in AAI overdrive mode may continue for a predetermined period of time, which, in one embodiment, does not to exceed 10 minutes. In another embodiment, this duration may be programmable. A mode switch may occur from the AAI overdrive mode to another mode if the AF episode is re-detected.

According to one aspect of the invention, an optional programmable ramp-up feature is provided. The pacing cycle length is gradually increased until a normal cycle is resumed, at which time the normal DDD pacing mode is resumed. The ramp-up time period may be programmable.

FIG. 1 is a block diagram of an implanted medical device (IMD) 100 that is configured to apply overdrive pacing according to an exemplary embodiment of the invention. Implanted medical device (IMD) 100 provides multi-site pacing to the atria and the ventricles of a patient's heart. IMD 100 includes a microprocessor 101 that controls IMD 100 in response to programmed instructions read from a storage device such as a read-only memory 102 via a data/address bus 108.

Microprocessor 101 is coupled to timing/control circuitry 106. Microprocessor controls the timing/control circuitry 106 to deliver pacing pulses to a patient at the appropriate times. These pacing pulses are delivered via two output circuits 110 and 112, which in one embodiment, includes output amplifiers and related circuitry. Timing/control circuitry 106 is also shown coupled to sense amplifiers 122 and 124. These amplifiers provide signals sensed via electrodes positioned within the body. For example, electrodes 114 and 116, which may be carried by a bipolar medical electrical lead, may be positioned within an atrium to sense atrial signals. Similarly, electrodes 118 and 120 may be carried by a lead positioned within a ventricle. It may be noted that although FIG. 1 illustrates the use of bipolar leads, unipolar leads may be used in the alternative. In that instance, signals are sensed between an electrode on a lead and a common electrode which is generally part of the device housing as is known in the art.

Additional electrodes and/or physiological sensors may be coupled to the sense amplifiers, as shown by additional signal line 128. Switch matrix 126 selectively couples the input and output circuits and the various electrodes.

The system of FIG. 1 is further shown to include a random access memory (RAM) 104, which may be used to store physiological signal data. For example, data obtained from tachyarrhythrnia episodes may be stored within (RAM). This data may be used by microprocessor 101 for therapy delivery and diagnostic purposes. This data may be transferred to an external device such as a programmer via telemetry circuit 130 and antenna 132 for use by a clinician, storage in a patient record, or other diagnostic and therapy related purposes. The telemetry circuit may further be used to transfer operating parameters, patient data, and other information to the IMD. In the context of the current invention, parameters associated with the novel pacing mode described herein may be programmed via the telemetry circuit.

FIG. 1 further illustrates a defibrillation circuit 140. This type of circuit may include high-voltage capacitors, charging circuits, and other logic as is known in the art. This circuit delivers high-voltage defibrillation and/or cardioversion shocks to a patient under the control of microprocessor 101.

The embodiment of FIG. 1 described above is purely exemplary, and those skilled in the art will recognize that many alternative arrangements and embodiments may be contemplated within the scope of the invention. For example, any of the circuits may be implemented with discrete or integrated digital systems, or another combination of digital and analog circuitry. In one implementation, microprocessor 101 may be replaced by a state machine or another processing circuit. For a more detailed discussion of the components of IMD 100 and different site-pacing and site-sensing configurations, reference is made to U.S. Pat. No. 6,185,459 to *Mehra* et al., which is assigned to the assignee of the present invention and which is incorporated herein by reference.

In the embodiment of FIG. 1, microprocessor 101 and timing/control circuitry 106 control pacing in various modes, including DDD, DVI, VDD, DDI pacing modes. Timing/control circuitry 106 also uses amplifier 122 to sense atrial depolarizations and amplifier 124 to sense ventricular depolarizations.

Upon sensing an arrhythmia, microprocessor 101 selects therapy to treat the arrhythmia according to a predetermined therapy regimen. This may include activating defibrillation circuit 140 to initiate charging of high voltage capacitors via a charging circuit (not shown). Timing/control circuitry 106 controls the time that defibrillation circuit 140 delivers the electrical cardioverting therapy to the patient. In this example, defibrillation circuit 140 can deliver the high-voltage therapy to an atrium via a high-voltage electrode 142 after an atrial arrhythmia is detected by electrode pair 114 and 116. The high-voltage shock may be delivered between the high-voltage electrode 142 and housing of the device, for instance, in attempt to terminate the arrhythmia. Defibrillation circuit could further be coupled to one or more additional high-voltage electrodes such as electrode 144 positioned within a ventricle.

If desired, arrhythmia therapy may include delivery of one or more defibrillation or cardioversion shocks. Alternatively, or in addition to, these shocks, anti-tachy pacing (ATP) therapy may be delivered as is known in the art. If desired, a combination of these therapies may be delivered using a tiered therapy approach. Following this predetermined therapy in response to the detected AF episode, atrial overdrive therapy according to the current invention may be delivered to a patient.

Figure 2:
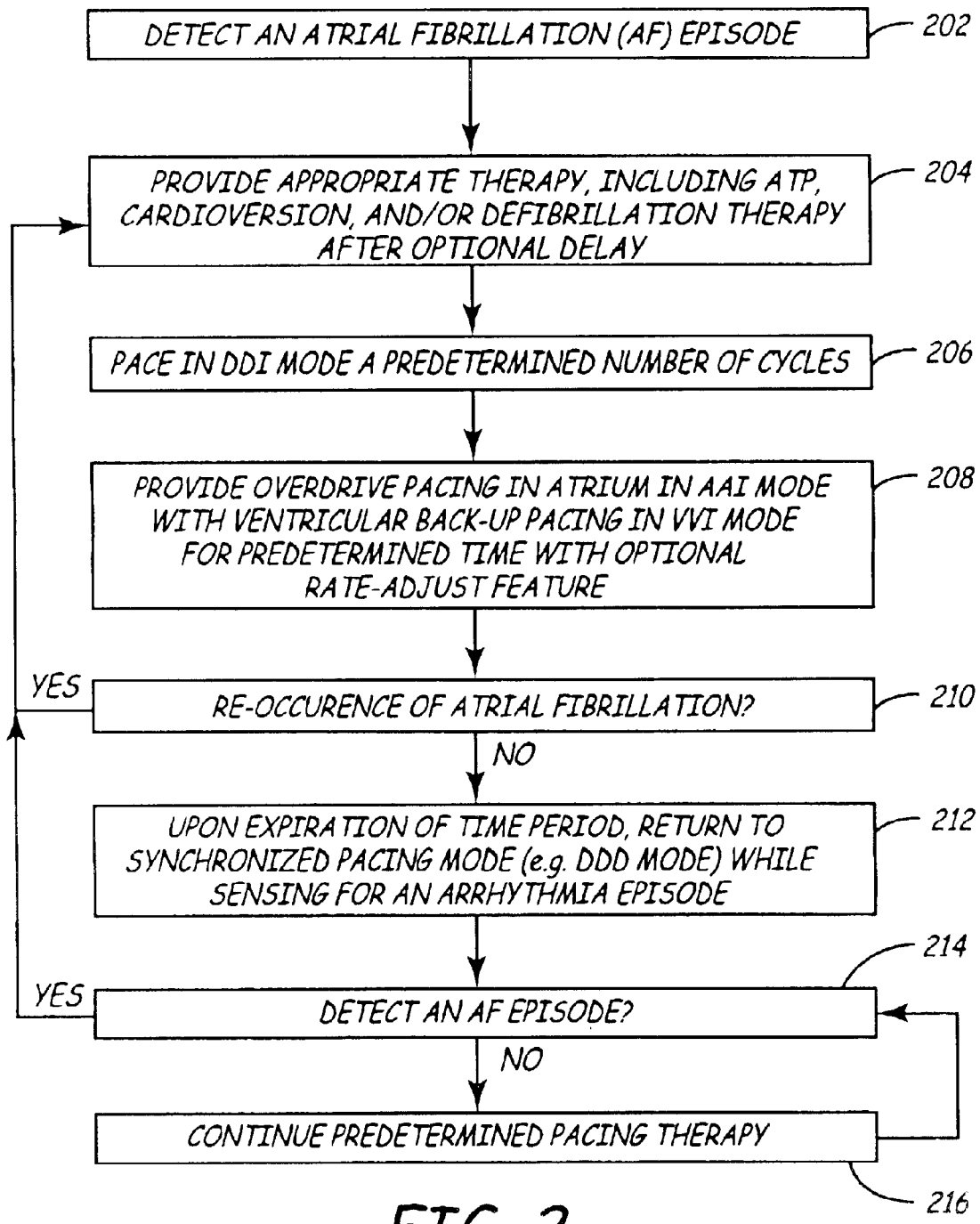
FIG. 2 is a flow diagram illustrating the manner of using atrial overdrive pacing, triggered by an electrical therapy, to prevent recurrence of atrial fibrillation according to an example embodiment of the invention.

FIG. 2 is a flow diagram illustrating the manner of using atrial overdrive pacing to prevent early recurrence of atrial fibrillation (ERAF) according to an exemplary embodiment of the invention. At step 202, IMD 100 detects an atrial fibrillation episode in an atrium of a patient's heart. At step 204, in response to detecting the atrial fibrillation, EMD 100 applies appropriate therapy to the atrium. This therapy may include delivering anti-tachy pacing (ATP), cardioversion, and/or defibrillation therapy to the atrium. At step 206, in response to the electrical cardioverting therapy, the IMD 100 may optionally enter DDI mode for a predetermined number of cardiac cycles, which in the preferred embodiment is one cycle. While pacing in DDI mode, the escape interval can be any pre-selected value, but in one embodiment this interval is 1200 milliseconds.

In one embodiment, pacing in DDI mode is initiated after a pre-selected delay, which may be about 500 msec. In another embodiment, this pacing can be initiated immediately following therapy delivery.

After pacing in DDI mode for the predetermined number of cycles, IMD 100 commences pacing the atrium with an atrial overdrive pacing therapy in AAI mode, as shown in step 208. Such overdrive pacing paces the heart at a rate that is faster than the intrinsic heart rate. Generally, the cycle time of such pacing will be between 500 ms and 1000 ms. During delivery of atrial overdrive pacing, backup ventricular pacing in VVI mode is provided for patients having AV block. Such pacing in AAI mode may continue for a predetermined period of time. If desired, an optional rate-adjust feature may be enabled so that the atrial pacing rate gradually decreases over time. Eventually, the rate reaches that which may be sustained during normal operations. In this embodiment, when the non-elevated, predetermined rate has been reached, the device switches to DDD mode.

During pacing at the elevated rate, detection for re-occurrence of AF is performed, as illustrated in step 210. If AF is detected, appropriate therapy delivery is performed based on a pre-programmed therapy regimen, as indicated by block 204. In one embodiment, this redetection causes a mode switch to DDI mode at a pre-programmed pacing rate. This may be followed by re-delivery of a high-voltage shock, or ATP therapy.

Otherwise, upon expiration of the predetermined time period, AAI overdrive pacing is discontinued, and pacing in a synchronized mode such as DDD mode is re-initiated. This is shown in step 212. Detection for AF is on-going while the predetermined pacing therapy in the synchronized mode is provided, as shown by steps 214 and 216. If AF re-occurrence is detected, execution continues with step 204.

In another related embodiment, IMD 100 can be programmed such that the pacing algorithm includes a pacing ramp up and a pacing ramp down sequence before the predetermined time of the atrial overdrive therapy expires. For example, in step 208, the pacing rate progressively decreases the overdrive pacing cycle length to a predetermined minimum cycle length, then increases the cycle length in the manner discussed above. This rate change may involve cycle-length changes of 25–50 msec every 30–60 seconds.

In yet another embodiment, the pacing algorithm is configurable such that IMD 100 exhibits a constant high atrial overdrive pacing rate for a predetermined time. In one embodiment, this time is selected as any time less than 10 minutes. This implementation thereby increases the likelihood of suppressing ectopic atrial activity.

Various modifications, equivalent processes, as well as numerous structures to which the present invention may be applicable will be readily apparent to those of skill in the art to which the present invention is directed upon review of the present specification. The claims are intended to cover such modifications and devices.

What is claimed is:

1. A method of preventing recurrence of atrial fibrillation (AF) in a heart, comprising:
    a.) delivering a predetermined therapy to terminate AF; and
    b.) pacing the atrium at a pacing rate that is higher than an intrinsic rate immediately following therapy delivery of step a.).

2. The method of claim 1, wherein step b.) includes providing backup ventricular pacing to a ventricle in VVI mode.

3. The method of claim 2, wherein the predetermined therapy to terminate AF is selected from the group consisting of cardioversion, defibrillation, and anti-tachy pacing (ATP) therapy.

4. The method of claim 3, and further including providing pacing in DDI mode for a predetermined number of cardiac cycles prior to step b.).

5. The method of claim 4, wherein the predetermined number of cardiac cycles is one cardiac cycle.

6. The method of claim 4, wherein providing pacing in DDI mode is initiated substantially immediately following step a.).

7. The method of claim 4, wherein providing pacing in DDI mode is initiated after a predetermined time period has elapsed following step a.).

8. The method of claim 2, wherein pacing according to step b.) is continued for a predetermined programmable time interval.

9. The method of claim 2, wherein pacing according to step b.) is performed using rate adjustment.

10. The method of claim 9, wherein the rate adjustment includes decreasing the pacing rate to a predetermined rate that can be sustained.

11. The method of claim 8, and further including initiating pacing to the atrium and ventricle in a synchronized mode after step b.) has been continued for the predetermined programmable time interval.

12. The method of claim 11, wherein the synchronized mode is DDD mode.

13. The method of claim 2, and further including discontinuing step b.) if AF is detected.

14. The method of claim 8, wherein the predetermined programmable time interval is selected to be between above 0.5 to about 10 minutes.

15. The method of claim 9, wherein rate adjustment includes adjusting a pacing cycle length in increments of 25–50 msec every 30–60 seconds for a selected time period.

16. A method of preventing atrial fibrillation recurrence with an implanted medical device comprising:
    in response to a first atrial fibrillation event in an atrium of a heart, applying an electrical cardioverting therapy to the atrium; and
    in response to the electrical card cardioverting therapy, pacing the heart with an atrial overdrive pacing therapy and switching the implanted medical device to a cardiac sensing mode that senses the atrium and a ventricle, wherein the implanted medical device is preprogrammed before the first atrial fibrillation event to automatically switch to the cardiac sensing mode.

17. The method of claim 16, wherein the electrical cardioverting therapy triggers the atrial overdrive pacing therapy and automatic switching to the cardiac sensing mode, wherein the cardiac sensing mode includes sensing and pacing the atrium and ventricle.

18. The method of claim 17, further comprising the steps of:
   while in the cardiac sensing mode, pacing the atrium in an atria inhibited (AAI) mode and pacing the ventricle in the heart in a backup ventricular pacing mode for a predetermined period of time and, after the predetermined period of time, returning to a pacing mode wherein the atrium and the ventricle are synchronized;
   during atrial overdrive pacing, sensing for a second atrial fibrillation event in the atrium; and
   in response to sensing the second atrial fibrillation event, stopping the atrial overdrive pacing therapy and switching the implanted device to the cardiac sensing mode and commencing a cardiac sensing mode pacing therapy.

19. The method of claim 16, wherein the step of pacing the heart with the atrial overdrive therapy includes pacing for a duration of between 0.5 to about 10 minutes.

20. The method of claim 16, wherein the step of pacing the heart with the atrial overdrive therapy includes pacing at a high rate for the duration, therein suppressing ectopic atrial activity.

21. The method of claim 16, wherein the step of pacing the heart with the atrial overdrive therapy includes ramping up an atrial overdrive cycle length in increments of 25–50 msec every 30–60 seconds for a selected time period.

22. The method of claim 16, further comprising the step of delaying the pacing with the atrial overdrive therapy for a programmed time period after applying the electrical therapy.

23. A system for preventing atrial fibrillation recurrence comprising:
   a therapy circuit to delivery therapy in response to detected atrial fibrillation; and
   a control circuit coupled to the therapy circuit to control delivery of pacing to an atrium in AAI mode at a rate faster than the intrinsic rate immediately following the therapy delivery.

24. The system of claim 23, wherein the control circuit further control delivery of pacing to a ventricle in VVI mode to provide ventricular backup pacing.

25. A method of preventing recurrence of atrial fibrillation (AF) in a heart, comprising:
   a.) delivering a predetermined therapy to terminate AF; and
   b.) pacing the atrium at a pacing rate that is higher than an intrinsic rate following therapy delivery of step a.), wherein step b.) includes providing backup ventricular pacing to a ventricle in VVI mode.

26. A system for preventing atrial fibrillation recurrence comprising:
   a therapy circuit to delivery therapy in response to detected atrial fibrillation; and
   a control circuit coupled to the therapy circuit to control delivery of pacing to an atrium in AAI mode at a rate faster than the intrinsic rate following the therapy delivery, wherein the control circuit further control delivery of pacing to a ventricle in VVI mode to provide ventricular backup pacing.

* * * * *